United States Patent [19]
Murray

[11] Patent Number: 5,510,306
[45] Date of Patent: Apr. 23, 1996

[54] PROCESS FOR ISOMERIZING LINEAR OLEFINS TO ISOOLEFINS

[75] Inventor: Brendan D. Murray, Houston, Tex.

[73] Assignee: Shell Oil Company, Houston, Tex.

[21] Appl. No.: 175,004

[22] Filed: Dec. 29, 1993

[51] Int. Cl.[6] .................................................. B01J 29/06
[52] U.S. Cl. .............................. 502/64; 502/68; 585/666; 585/671
[58] Field of Search ........................................ 502/64, 68

[56] References Cited

U.S. PATENT DOCUMENTS

| | | |
|---|---|---|
| 2,217,252 | 6/1938 | Hoog . |
| 3,326,818 | 6/1967 | Gladrow et al. . |
| 3,691,099 | 9/1972 | Young . |
| 3,917,808 | 11/1975 | Leach et al. . |
| 4,107,087 | 8/1978 | Pessimisis . |
| 4,132,669 | 1/1979 | Choca et al. . |
| 4,174,301 | 11/1979 | Choca et al. . |
| 4,239,655 | 12/1980 | Inoue et al. . |
| 4,335,019 | 6/1982 | Bowes et al. . |
| 4,388,177 | 6/1983 | Bowes et al. . |
| 4,402,865 | 9/1983 | Blakely . |
| 4,795,623 | 1/1989 | Evans . |
| 4,942,027 | 7/1990 | Evans . |
| 5,242,676 | 9/1993 | Apelian et al. . |
| 5,321,194 | 6/1994 | Apelian et al. . |

FOREIGN PATENT DOCUMENTS

| | | |
|---|---|---|
| 0501577A1 | 2/1992 | European Pat. Off. . |
| 0523838A2 | 3/1992 | European Pat. Off. . |
| 91/04943 | 4/1991 | WIPO . |

*Primary Examiner*—Sharon Gibson

[57] ABSTRACT

An active and stable catalyst for isomerizing linear olefins to methyl branched isoolefins is provided by (a) mixing (i) a zeolite powder containing at least one zeolite with at least one one-dimensional pore structure having pore size small enough to retard by-product dimerization and coke formation and large enough to permit entry of the linear olefin and allow formation of the methyl branched isoolefin, (ii) an alumina-containing binder, (iii) water, (iv) at least one acid selected from monocarboxylic acids and inorganic acids and (v) at least one polycarboxylic acid; (b) forming a pellet of the mixture; and (c) calcining the pellet. The resulting catalyst has superior selectivity, higher maximum product concentration in the product stream and longer run length for isomerizing linear olefins to their corresponding isoolefins.

13 Claims, No Drawings

1

PROCESS FOR ISOMERIZING LINEAR OLEFINS TO ISOOLEFINS

FIELD OF INVENTION

This invention relates to olefin isomerization catalysts. In a specific aspect, the invention relates to a process to prepare improved olefin isomerization catalysts for isomerizing linear olefins to methyl branched isoolefins.

BACKGROUND OF THE INVENTION

Increasing demand for high octane gasoline blended with lower aliphatic alkyl ethers such as octane boosters and supplementary fuels has created a significant demand for isoalkylethers, especially the $C_5$ to $C_7$ methyl, ethyl and isopropyl-t-alkyl ethers, such as methyl t-butyl ether, ethyl t-butyl ether, t-amyl methyl ether and t-amyl ethyl ether. Consequently, there is an increasing demand for the corresponding isoolefin starting materials such as isobutene, isoamylenes and isohexenes.

To obtain isoolefins, it is desirable to convert an olefin or alkene such as normal butene, to a methyl branched alkene, for example isobutylene, by mechanisms such as structural isomerization. Such converted isoolefins then can be reacted further, such as by polymerization, etherification or oxidation, to form useful products. Normal olefins containing four carbon atoms (1-butene, trans-2-butene and cis-2-butene) and five carbon atoms (1-pentene, trans-2-pentene, and cis-2-pentene) are relatively inexpensive starting compounds. Conventionally, butenes and amylenes, including to a minor extent isobutylene and isoamylene, are obtained as a by-product from refinery and petrochemical processes such as catalytic and thermal cracking units. Butenes are also conveniently obtained from butadiene via selective hydrogenation.

Zeolite materials, both natural and synthetic, are known to have catalytic properties for many hydrocarbon processes. Zeolites typically are ordered porous crystalline aluminosilicates having a definite structure with cavities interconnected by channels. The cavities and channels throughout the crystalline material generally can be of such a size to allow selective separation of hydrocarbons. Such hydrocarbon separation by the crystalline aluminosilicates essentially depends on discrimination between molecular dimensions. Consequently, these materials in many instances are known in the art as "molecular sieves" and are used, in addition to catalytic properties, for certain selective adsorptive processes. Zeolite molecular sieves are discussed in great detail in D. W. Breck, *Zeolite Molecular Sieves*, Robert E. Krieger Publishing Company, Malabar, Fla. (1984).

Generally, the term "zeolite" includes a wide variety of both natural and synthetic positive ion-containing 5 crystalline aluminosilicate materials, including molecular sieves. They generally are characterized as crystalline aluminosilicates which comprise networks of $SiO_4$ and $Al_4$ tetrahedra in which silicon and aluminum atoms are cross-linked in a three-dimensional framework by sharing of oxygen atoms. This framework structure contains cavities and channels or interconnected voids that are occupied by cations, such as sodium, potassium, ammonium, hydrogen, magnesium, calcium, and water molecules. The water may be removed reversibly, such as by heating, which leaves a crystalline host structure available for catalytic activity. The term "zeolite" in this specification is not limited to crystalline aluminosilicates. The term as used herein also includes silicoaluminophosphates (SAPO), metal integrated aluminophosphates (MeAPO and ELAPO), metal integrated silicoaluminophosphates (MeAPSO and ELAPSO). The MeAPO, MeAPSO, ELAPO, and ELAPSO families have additional elements included in their framework. For example, Me represents the elements Co, Fe, Mg, Mn, or Zn, and EL represents the elements Li, Be, Ga, Ge, As, or Ti. An alternative definition would be "zeolitic type molecular sieve" to encompass the materials useful for this invention.

Developments in the art have resulted in formation of many synthetic zeolitic crystalline materials. Crystalline aluminosilicates are the most prevalent and, as described in the patent literature and in the published journals, are designated by letters or other convenient symbols. Various zeolites which have been specifically named and described are, for example, Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite ZSM-23 (U.S. Pat. No. 4,076,842), Zeolite ZSM-35 (U.S. Pat. Nos. 4,016,245 and 5,190,736), Zeolite ZSM-48 (U.S. Pat. No. 4,375,573), Zeolite NU-1 (U.S. Pat. No. 4,060,590) and others. Various ferrierite zeolites including the hydrogen form of ferrierite, are described in U.S. Pat. Nos. 3,933,974, 4,000,248 and 4,942,027 and patents cited therein. SAPO-type catalysts are described in U.S. Pat. No. 4,440,871. MeAPO type catalysts are described in U.S. Pat. Nos. 4,544,143 and 4,567,029; ELAPO catalysts are described in U.S. Pat. No. 4,500,651, and ELAPSO catalysts are described in European Pat. Application 159,624.

Two general classes of catalysts have been disclosed as particularly useful for isomerizing a linear olefin to the corresponding methyl branched isoolefin. These include the porous, non-crystalline, refractory oxide-based catalysts and the zeolitic-based catalysts.

Illustrative of the porous, non-crystalline refractory oxide catalysts are those described in U.S. Pat. Nos. 4,434,315, 5,043,523, 3,531,542, 3,381,052, 3,444,096, 4,038,337, 3,663,453, British Patent No. 2,060,424 and in an article by V. R. Choudhary and L. K. Doraiswamy, "Isomerization of n-Butene to Isobutene, I. Selection of Catalyst by Group Screening," Journal of Catalysis, volume 23, pages 54–60, 1971. All of these catalysts deactivate rapidly. According to the examples in British Patent No. 2,060,424, run life can be as short as 1 to 2 hours. Often, it is necessary to add steam and halogen compounds to prolong the catalyst run life. German specification No. 3,000,650-A states that the run life can be increased to approximately 50 hours by these methods although this is still less than desirable.

With regard to the zeolitic-based catalysts, the most significant use has involved large pore zeolites or zeolites having two or more-dimensional interconnecting channels. Illustrative of these materials are U.S. Pat. Nos. 4,503,282, 5,227,569, 4,435,311, and 4,392,003.

More recently, European Patent Publication Number 523, 838 A2, published Jan. 20, 1993, has disclosed a process for structurally isomerizing a linear olefin to its corresponding methyl branched isoolefin using as a catalyst a zeolite with one or more one-dimensional pore structure having a pore size small enough to retard by-product dimerization and coke formation within the pore structure and large enough to permit entry of the linear olefin and allow formation of the methyl branched isoolefin (i.e. medium or intermediate pore zeolites). These catalysts are formed by blending a finely divided crystalline zeolite with a binder material and mulling the blended mixture by adding water and acetic acid. The resulting mixtures are then shaped, dried and calcined to form the catalyst composition.

However, it is desirable to have a more active and stable catalyst composition to obtain increased efficiency or overall yield of the desired isoolefins. Such an increase can be obtained by increase in run length, higher selectivity and/or higher activity of the catalyst used in the olefin isomerization process.

It is therefore an object of the present invention to provide a medium pore zeolite catalyzed process for structurally isomerizing a linear olefin to its corresponding methyl branched isoolefin with improved stability, efficiency and/or yield. It is another object of the present invention to provide a more stable catalyst composition useful in structurally isomerizing a linear olefin to isoolefins.

SUMMARY OF THE INVENTION

According to the invention, a process for preparing a catalyst for structurally isomerizing a linear olefin of at least 4 carbon atoms to its corresponding methyl branched isoolefin is provided and the catalyst composition prepared by the process is provided. Such catalyst composition is provided by a process comprising:

(a) mixing (i) a zeolite powder comprising at least one zeolite with at least one one-dimensional pore structure having pore size small enough to retard by-product dimerization of the linear olefin and coke formation within the pore structure and large enough to permit entry of the linear olefin and allow formation of the methyl branched isoolefin, (ii) an alumina-containing binder, (iii) water, (iv) at least one monocarboxylic acid or an inorganic acid and (v) at least one organic acid having at least two carboxylic acid groups thereby producing a mixture;

(b) forming a pellet of said mixture; and (c) calcining said pellet at a temperature of from about 200° C. to about 700° C.

DETAILED DESCRIPTION OF THE INVENTION

It has been found that by preparing the catalyst composition by blending a finely divided crystalline zeolite with a binder material and thoroughly mixing the blended mixture with a conventional peptizing monocarboxylic acid or an inorganic acid and a promoting organic acid having at least two carboxylic acid groups, the resulting catalyst composition after forming and calcining has superior activity, selectivity and run length for structurally isomerizing linear olefins to isoolefins. By using a combination of two types of acids in the preparation of the catalyst, it produces a catalyst composition that is more active and stable.

Catalyst

The isomerizing catalysts used in the instant process contain a zeolite as hereinafter defined, a binder and optionally a coke-oxidation promoting metal.

The zeolite used in the isomerization catalyst of this invention comprises a zeolite having one-dimensional pore structures with a pore size ranging from greater than about 0.42 nm and less than about 0.7 nm. Zeolites with this specified pore size are typically referred to as medium or intermediate pore zeolites and typically have a 10-member (or puckered 12-member) ring channel structure in one dimension and an 9-member or less (small pore) in the other dimensions, if any. For purposes of this invention, a one-dimensional pore structure is considered one in which the channels having the desired pore size do not interconnect with other channels of similar or larger dimensions; it may also be considered alternatively as a channel pore structure (see U.S. Pat. No. 3,864,283) or uni-directional sieve.

The zeolite catalyst preferably comprises substantially only zeolites with the specified pore size in one dimension. Zeolites having pore sizes greater than 0.7 nm are susceptible to unwanted aromatization, oligomerization, alkylation, coking and by-product formation. Further, two or three-dimensional zeolites having a pore size greater than 0.42 nm in two or more dimensions permit dimerization and trimerization of the alkene. Hence, zeolites having a pore diameter bigger than about 0.7 nm in any dimension or having a two or three-dimensional pore structure in which any two of the dimensions has a pore size greater than about 0.42 nm are excluded as part of this invention. Zeolites that contain only small pores (i.e., less than about 0.42 nm) do not allow for diffusion of the methyl branched isoolefin product.

Examples of zeolites that can be used in the processes of this invention, which have one-dimensional pore structures with a pore size between about 0.42 nm and 0.7 nm, include the hydrogen form of ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite. The isotypic structures of these frameworks, known under other names, are considered to be equivalent. An overview describing the framework compositions of many of these zeolites is provided in *New Developments in Zeolite Science Technology*, "Aluminophosphate Molecular Sieves and the Periodic Table," Flanigen et al. (Kodansha Ltd., Tokyo, Japan 1986).

Many natural zeolites such as ferrierite, heulandite and stilbite feature a one-dimensional pore structure with a pore size at or slightly smaller than about 0.42 nm diameter. These same zeolites can be converted to zeolites with the desired larger pore sizes by removing the associated alkali metal or alkaline earth metal by methods known in the art, such as ammonium ion exchange, optionally followed by calcination, to yield the zeolite in substantially its hydrogen form. See e.g., U.S. Pat. Nos. 4,795,623 and 4,942,027 incorporated herein by reference. Replacing the associated alkali or alkaline earth metal with the hydrogen form correspondingly enlarges the pore diameter. It is understood that the pore diameter or "size" shall mean the effective pore diameter or size for diffusion. Alternatively, natural zeolites with too large a pore size, such as mordenite, can be altered by substituting the alkali metal with larger ions, such as larger alkaline earth metals to reduce the pore size and thus become useful for the processes of this invention.

Particularly preferred zeolites are those having the ferrierite isotypic framework structure (or homeotypic). See the *Atlas of Zeolite Structure Types*, by W. M. Meier and D. H. Olson, published by Butterworth-Heinemann, third revised edition, 1992, page 98. The prominent structural features of ferrierite found by x-ray crystallography are parallel channels in the alumino-silicate framework which are roughly elliptical in cross-section. Examples of such zeolites having the ferrierite isotypic framework structure include natural and synthetic ferrierite (can be orthorhombic or monoclinic), Sr-D, FU-9 (EP B-55,529), ISI-6 (U.S. Pat. No. 4,578,259), NU-23 (E.P. A-103,981), ZSM-35 (U.S. Pat. No. 4,016,245)

and ZSM-38 (U.S. Pat. No. 4,375,573). The hydrogen form of ferrierite (H-ferrierite) is the most preferred zeolite and considered to be comprised substantially of a one-dimensional structure having an elliptical pore size (>0.54 nm and >0.42 nm) large enough to permit entry of the linear olefin and diffusion of the methyl branched isoolefin and small enough to retard coke formation. Methods for preparing various H-ferrierite are described in U.S. Pat. Nos. 4,251,499, 4,795,623 and 4,942,027.

Exemplary of zeolites that are not useful for the processes of this invention include ZSM-5, ZSM-20, Beta, erionite, zeolite Y, hydrogen form of mordenite, and faujasite.

The zeolite catalyst used in the isomerization processes of this invention are combined with a refractory oxide that serves as a binder material. Suitable refractory oxides include natural clays, such as bentonite, montmorillonite, attapulgite, and kaolin; alumina; silica; silica-alumina; hydrated alumina; titania; zirconia and mixtures thereof. The weight ratio of zeolite to binder material suitably ranges from about 60:40 to about 99.5:0.5, preferably from about 75:25 to about 99:1, more preferably from about 80:20 to about 98:2 and most preferably from about 85:15 to about 95:5 (anhydrous basis). Preferably the binder is an alumina.

Binders useful in preparing the catalysts are any of the conventional alumina-containing binders known in the art for preparing catalysts and include, for example, the aluminas, the silica-aluminas and the clays. For purpose of the invention, alumina-containing binders include any of the alumina precursors including the hydrated forms of alumina such as bayerite, bohmite and gibbsite which upon calcination are converted to alumina ($Al_2O_3$). Preferred silica-aluminas are the amorphous silica-aluminas such as the aluminosilicate gels and sols. Non-limiting examples of the clays include bentonite, hectorite, kaolin, attapulgite and the like. The binders are provided in any convenient form, such as powders, slurries, gels or sols. When the binders are provided as slurries, gels or sols, at least part of the water used in the mulling step will be found as part of the slurry, gel or sol.

Preferred binders are aluminas, such as pseudoboehmite, gamma and bayerite aluminas. These binders are readily available commercially and are used to manufacture alumina-based catalysts. LaRoche Chemicals, through its VERSAL® family of aluminas and Vista Chemical Company, through its CATAPAL® aluminas, provide suitable alumina powders which can be used as binders in preparing the instant catalysts. Preferred alumina binders to be used in the preparation of the catalyst, particularly when extrusion is utilized, are the high-dispersity alumina powders. Such high-dispersity aluminas have a dispersity of greater than 50% in a aqueous acid dispersion having an acid content of 0.4 milligram equivalents of acid (acetic) per gram of $Al_2O_3$. Such high-dispersity aluminas are exemplified by Vista's CATAPAL® D alumina.

At least one acid selected from monocarboxylic acids and inorganic acids and at least one organic acid with at least two carboxylic acid groups ("polycarboxylic acid") is used in the preparation of the catalyst. Preferred monocarboxylic acid includes monocarboxylic acid having substituted or unsubstituted hydrocarbyl group having 1 to 20 carbon atoms which can be aliphatic, cyclic or aromatic. Suitable substitution can be for example, a hydroxyl group. Preferred monocarboxylic acid includes, for example, acetic acid, formic acid, propionic acid, butyric acid, caproic acid, glycolic acid, lactic acid, hydroxylbutyric acid, hydroxycyclopentanoic acid, salicylic acid, mandelic acid, benzoic acid, and fatty acids. Preferred inorganic acid includes mineral acids such as nitric acid, phosphoric acid, sulfuric acid and hydrochloric acid. The preferred first acid is acetic acid, formic acid, glycolic acid and nitric acid.

The preferred polycarboxylic acid is an organic acid with two or more carboxylic acid groups attached through a carbon-carbon bond linkage to an hydrocarbyl segment. The linkage can be at any portion of the hydrocarbyl segment. The polycarboxylic acid preferably has an hydrocarbyl segment from 0 to 10 carbon atoms which can be aliphatic, cyclic or aromatic. The hydrocarbyl segment has 0 carbon atoms for oxalic acid with two carboxylic acid groups attached through the carbon-carbon bond. Examples of the polycarboxylic acids includes, for example, tartaric acid, citric acid, malic acid, oxalic acid, adipic acid, malonic acid, galactaric acid, 1,2-cyclopentane dicarboxylic acid, maleic acid, fumaric acid, itaconic acid, phthalic acid, terephthalic acid, phenylmalonic acid, hydroxyphtalic acid, dihydroxyfumaric acid, tricarballylic acid, benzene-1,3,5-tricarboxylic acid, isocitric acid, mucic acid and glucaric acid. The polycarboxylic acids can be any isomers of the above acids or any stereoisomers of the above acids. Polycarboxylic acids with at least two carboxylic acid groups and at least one hydroxyl group is more preferred. The most preferred second acids (i.e., polycarboxylic acids) are citric acid, tartaric acid and malic acid.

Optionally, coke oxidation promoting metals can be incorporated into the instant catalysts to promote the oxidation of coke in the presence of oxygen at a temperature greater about 250° C. While the term "metal(s)" is used herein in reference to the oxidation catalysts, these metals will not necessarily be in the zero-valent oxidation state and in many cases will be in the higher oxidation states. Thus, "metal(s)" can encompass the oxides as well as the metals.

Preferably the coke oxidation-promoting metal(s) used are transition and rare earth metals. More preferably the coke oxidation-promoting metals are selected from Groups IB, VB, VIB, VIIB and VIII of the transition metal series of the Periodic Table. Specifically preferred are Pd, Pt, Ni, Co, Mn, Ag and Cr. Most preferred are the Group VIII metals palladium and/or platinum.

The amount of metal introduced can be up to about 2% by weight, measured as the metal per total weight of the catalyst. When using platinum and/or palladium, smaller amounts of metals rather than larger amounts of metals incorporated into the zeolite/binder are preferred. Preferably platinum and/or palladium will range from about 5 ppm to about 3000 ppm by weight, basis metal, of the final catalyst.

The instant catalysts can be prepared by mixing a mixture of at least one zeolite as herein defined, alumina-containing binder, water, at least one monocarboxylic acid or inorganic acid and at least one polycarboxylic acid in a vessel or a container, forming a pellet of the mixed mixture and calcining the pellets at elevated temperatures. In one preferred embodiment zeolite powder and alumina-containing powder is mixed with water and one or more of monocarboxylic acid or inorganic acid (first acid) and one or more of polycarboxylic acid (second acid) and optionally one or more compounds of the coke-oxidation promoting metal and the resulting mixture (paste) is formed into a pellet. The coke-oxidation promoting metal may alternatively be impregnated. Preferably the pellet is formed by extrusion but can also be formed into catalytically useful shape by pressing hydrostatically or mechanically by pressing into die or mold. When extrusion is used optional extrusion aids such as cellulose derivatives, e.g., METHOCEL® F4M hydroxypropyl methylcellulose, can be utilized (manufactured by The Dow Chemical Company). The term "pellets" as used herein can be in any shape or form as long as the materials are consolidated. The formed pellets are calcined at a temperature ranging from a lower range of from about 200° C., preferably from about 300° C., more preferably from about 450° C., to an upper range of up to about 700° C., preferably up to about 600° C., more preferably up to about 525° C.

The ratio of the first acids to second acids is preferably within the range of about 1:60 to about 60:1, more preferably 1:10 to about 10:1. The amount of the first acid used is in an amount effective to peptize the mixture. Preferably the amount of the first acid used is from about 0.1 weight percent to about 6 weight percent, more preferably from about 0.5 weight percent to about 4 weight percent based on the combined weight of zeolite and alumina-containing binder (anhydrous solids basis). Aluminas with lower dispersibilities than Vista Catapal D may require greater amounts of acid to peptize them. The amount of the second acid used is in an amount effective to promote the catalytic activity of the catalyst which is from about 0.1 weight percent to about 6 weight percent, preferably from about 0.2 weight percent to about 4 weight percent based on the combined weight of zeolite and alumina-containing binder (anhydrous solids basis).

The mixture is mixed thoroughly or vigorously until the mixture appears uniform. The mixing can be performed by combining all of the components of the mixture at once or by adding the components of the mixture at different stages of mixing. The mixing can be accomplished by mulling. The term "mulling" is used herein to mean mixing of powders to which sufficient water has been added to form a thick paste and wherein the mixing is accompanied by shearing of the paste. Commercially available mullers such as the Lancaster Mix Muller and the Simpson Mix Muller can be used to carry out the mixing. A commercial blender such as a ribbon blender and/or a powder mill can also be used to carry out the mixing.

Optionally the coke-oxidation promoting metal can be impregnated to the formed pellet with a metals-containing solution instead of mixing in the paste mixture.

Hydrocarbon Feed Stream

The hydrocarbon feed useful for this invention contains at least one linear olefin. Typically, the linear olefin will contain at least four, preferably four to ten carbon atoms. Also considered a linear olefin for purposes of this invention is a compound containing a linear alkene segment with four to ten carbon atoms. It is believed that long chain linear alkenes and compounds containing long chain linear segments may penetrate the zeolite catalyst for a distance effective to allow isomerization. Thus, the entire molecule need not be small enough to fit entirely within the pore structure of the catalyst. The preferred feed contains butylene and/or amylene.

As used herein, n-butylene includes all forms of n-butylene, for example 1-butene and 2-butene, either trans-2-butene or cis-2-butene, and mixtures thereof. As used herein, n-amylene or n-pentene, includes 1-pentene, cis- or trans-2-pentene, or mixtures thereof. The n-butylene or n-amylene used in the processes of this invention is generally in the presence of other substances such as other hydrocarbons. Thus, a feedstream used in the process of the invention containing n-butylene or n-amylene also can contain other hydrocarbons such as alkanes, other olefins, diolefins such as butadiene, aromatics, hydrogen, and inert gases. Typically, the n-butene feedstream used in this invention contains about 10 to about 100 wt. % n-butene. For example, a fractionated hydrocarbon feedstream from a fluid catalytic cracking effluent stream generally contains about 20 to about 60 wt. % normal butene and a hydrocarbon effluent from an ethers processing unit, such as methyl-tert-butyl ether (MTBE) generally contains from 40 to about 100 wt. % n-butylene. Feed streams from steam crackers and catalyst crackers may also contain substantial amounts of alkanes, say, up to about 80 wt. %. Olefins obtained by selective hydrogenation of dienes, such as butadiene, may also be used.

As used herein, the term "olefin" can be alternatively referred to as "alkene"; the term "linear" can be alternatively referred to as "normal"; and the term "isoolefin" can be alternatively referred to as "methyl branched isoolefin." Similarly, butene and butylene refer to the same four carbon alkene; and pentene and amylene refer to the same five carbon alkene.

Isomerizing Conditions

In the processes of this invention, a hydrocarbon stream comprising at least one linear olefin is contacted with the catalytic zeolite under isomerizing conditions. Generally, in the processes of this invention, the hydrocarbon stream is contacted with the above-described zeolite catalyst in a vapor phase at a suitable reaction temperature, pressure and space velocity. Generally, suitable reaction conditions include a temperature of about 200° C. to about 650° C. preferably from about 320° C. to about 600° C., an olefin partial pressure of above about 0.5 atmosphere, and a total pressure of about 0.5 to about 10.0 atmospheres or higher, a hydrogen/hydrocarbon molar ratio of 0 to about 30 or higher, substantially free of water (i.e., less than about 2.0 wt % of the feed), and a hydrocarbon weight hourly space velocity (WHSV) of about 0.5 to about 100 $hr^{-1}$. These reactor streams can contain non-reactive diluents such as alkanes. The hydrogen can be added directly to the feed stream prior to introduction of the isomerization zone, or the hydrogen can be added directly to the isomerization zone.

The preferred reaction temperature will depend on a number of factors such as the pressure, the weight hourly space velocity and the feed composition, to name a few. Lower molecular weight olefins such as butenes are best isomerized at a temperature between about 200° C. –650° C. while higher molecular weight olefins are best isomerized at lower temperatures. Pentenes are best isomerized at a temperature between about 200° C. –550° C. and hexenes are best isomerized at a temperature between about 200° C. –500° C. Mixed butenes and pentenes are best isomerized at a temperature between about 200° C. –600° C. and mixed pentenes and hexenes are best isomerized at a temperature between about 200° C. –525° C. The use of a lower temperature may be advantageous when the olefin is easily cracked to lighter unwanted species at higher temperatures. It is also possible to achieve higher concentrations of desired products at lower temperatures due to the fact that higher equilibrium concentrations of the branched olefins are possible at lower temperatures.

In a typical butene isomerization process scheme, a butene vapor stream is contacted with such catalyst in a reactor at about 320° C. to about 650° C., at an olefin partial pressure of about 5 psia to about 50 psia and a total pressure of about 15 to about 100 psia, and at an olefin based WHSV of about 0.5 to about 50 $hr^{-1}$. Preferred isomerizing conditions are carried out at a temperature of between about 320° C. to 450° C., at atmospheric pressure, and an olefin based WHSV of between about 2 to about 25 $hr^{-1}$, more preferably between about 2 to about 15 $hr^{-1}$.

In a typical pentene isomerization process scheme, a pentene vapor stream is contacted with such catalyst in a reactor at about 250° C. to about 550° C., at an olefin partial pressure of about 3 psia to about 100 psia and a total pressure of about 15 to about 100 psia, and at an olefin based WHSV of about 1 to about 100 hr$^{-1}$. Preferred isomerizing conditions are carried out at a temperature of between about 300° C. to 425° C., at atmospheric pressure, and an olefin based WHSV of between about 2 to about 40 hr$^{-1}$.

For a mixed feed, reaction conditions between pentene and butene isomerization processes can be used depending on the desired product mix.

The process of the present invention can utilize a combination of zeolites with one or more one dimensional pore structures having a pore size small enough to retard by-products dimerization and coke formation with the pore structure large enough to permit entry of the linear olefin(s) and diffusion of the isoolefin product(s). These combinations can include pellets of mixed zeolites and stacked bed arrangements of catalysts such as, for example, ZSM-22 and/or ZSM-23 over ferrierite, ferrierite over ZSM-22 and/or ZSM-23, and ZSM-22 over ZSM-23. The stacked catalysts can be of the same shape and/or size or of different shape and/or size such as ⅛ inch trilobes over 1/32 inch cylinders for example.

In a particularly preferred embodiment a process for structurally isomerizing a linear olefin of at least 4 carbon atoms to its corresponding methyl branched isoolefin is provided, comprising contacting at a temperature of from about 200° C. to about 650° C. a hydrocarbon feed stream containing at least one said linear olefin with an isomerizing catalyst produced by the process which comprises:

(a) mixing
  (i) a zeolite powder comprising at least one zeolite with at least one one-dimensional pore structure having pore size small enough to retard by-product dimerization and coke formation within the pore structure and large enough to permit entry of the linear olefin and allow formation of the methyl branched isoolefin,
  (ii) an alumina-containing binder,
  (iii) water, and
  (iv) an effective amount of an acid comprising at least one polycarboxylic acid to peptize the zeolite powder, the binder or a mixture thereof thereby producing a mixture;

(b) forming a pellet of said mixture; and (c) calcining said pellet at a temperature of from about 200° C. to about 700° C. Preferably the polycarboxylic acid is present in an amount of from about 0.1 weight percent to about 6 weight percent, based on (i) and (ii). More preferably the acid contains component (1) one or more monocarboxylic acids or inorganic acids and (2) one or more polycarboxylic acids.

Regeneration Conditions

During the process, some coke will be formed on the surface of the catalyst. The surface of the catalyst where the coke builds up can be on the outer surface and/or on the surface of the inner channels and/or pores of the catalyst. Therefore, it is advantageous to regenerate the catalyst when at least 2%, preferably at least 5%, more preferably at least 10%, but before 30%, preferably before 25%, most preferably before 20 % by weight of coke build-up (basis uncoked catalyst).

When the build up of coke on the catalyst reaches a point where it needs to be regenerated, the hydrocarbon feed to the catalyst is stopped, any strippable hydrocarbon on the catalyst is stripped with hot gas (e.g. nitrogen and/or hydrogen) and the catalyst is then regenerated by subjecting it to heat treatment with an oxygen-containing gas. Stripping may be carried out at high pressure, under vacuum, or by cycling the reactor by pressurizing and depressurizing. Stripping may be combined with regeneration. For example, in a butene isomerization process, the butene feed can be stopped and replaced with hydrogen feed during stripping and then replaced with an oxygen-containing gas stream for regeneration.

Regeneration is carried out under conditions effective to substantially burn off the coke on the surface of the coked catalyst. The coke is substantially burned off when more than about 80% by weight of the coke is removed based on the initial total coke level when olefin isomerization or the linear olefin feed is stopped. Typical regeneration conditions include temperatures ranging from about 250° C. to about 565° C., preferably to about 530° C., with pressures ranging from about 1 atmosphere to about 100 atmospheres. Regeneration temperatures are measured as average reactor environment temperatures (i.e., hulk gas phase temperatures).

The oxygen partial pressure relative to total system pressure is typically within the range of from about 0.001 atmosphere to shout 40 atmospheres. Preferably the oxygen-containing gas is air, optionally diluted with additional nitrogen, carbon dioxide or hydrocarbon combustion products. Exotherms in the catalyst bed during regeneration can he avoided by a suitable increasing of the temperature or by an increasing of the oxygen concentration in the oxygen-containing gas or both during the regeneration process in order to obtain a steady burn of the coke. Typical regeneration times will range from about 5 to about 200 hours.

In the process of the invention the time between regeneration is prolonged due to the-stability of the catalyst (i.e., longer run length). Therefore, fewer regenerations need to be carried out for a given quantity of the isoolefin products produced.

The isomerization and/or regeneration process can be carried out in a packed bed reactor, a fixed bed, fluidized bed reactor or a moving bed reactor. The bed of the catalyst can move upward or downward. The isomerization process and the regeneration process may be carried out in the same bed or in separate beds.

Illustrative Embodiment

The following illustrative embodiments are provided to illustrate the invention and are not intended to be construed to limiting the inventions to such embodiments.

Preparation of the Catalyst

The following examples illustrate methods of preparation of catalysts of the invention useful for isomerizing olefins to isoolefins. An ammonium-ferrierite having a molar silica to alumina ratio of 62:1, a surface area of 369 square meters per gram (P/Po=0.03), a soda content of 480 ppm and n-hexane sorption capacity of 7.3 g per 100 g of zeolite was used as the starting zeolite in the following examples.

The catalyst components were mulled using a Lancaster mix muller. The mulled catalyst material was extruded using an 1 inch or a 2.25 inch Bonnot pin barrel extruder.

The binder utilized was CATAPAL® D alumina from Vista Chemical Company and METHOCEL®(R) F4M hydroxypropyl methylcellulose from The Dow Chemical Company was used as an extrusion aid. The acids were obtained from The Aldrich Chemical Company.

Catalyst A

Catalyst A was prepared as a comparative example using 1 weight percent acetic acid and no polycarboxylic acid in the catalyst preparation.

The Lancaster mix muller was loaded with 632 grams of ammonium-ferrierite (3.4% loss on ignition ("LOI")) and 92 grams of CATAPAL® D alumina (LOI of 26.2%). The alumina was blended with the ferrierite for 5 minutes during which time 156 milliliters of de-ionized water was added. A mixture of 6.8 grams glacial acetic acid and 156 milliliters of de-ionized water was added slowly to the muller in order to peptize the alumina. The mixture was mix-mulled for 10 minutes. 0.20 Grams of tetraammine palladium nitrate in 156 grams of de-ionized water were then added slowly as the mixture was mulled for a period of 5 additional minutes. Ten grams of METHOCELe®(R) F4M hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a stainless steel die plate with 1/16" holes.

Catalyst B

Catalyst B was prepared as a comparative example using 2 weight percent acetic acid and no polycarboxylic acid in the catalyst preparation.

The Lancaster mix muller was loaded with 64.5 grams of ammonium-ferrierite (5.4% LOI) and 9.1 grams of CATAPAL® D alumina (LOI of 25.7%). The alumina was blended with the ferrierite for 5 minutes during which time 15 milliliters of de-ionized water was added. A mixture of 1.4 grams of glacial acetic acid and 15 milliliters of de-ionized water was added slowly to the muller in order to peptize the alumina. The mixture was mix-mulled for 10 minutes. 0.02 Grams of tetraammine palladium nitrate in 15 grams of de-ionized water was then added slowly as the mixture was mulled for a period of 5 additional minutes. One gram of METHOCEL®(R) F4M hydroxypropyl methylcellulose was added and the zeolite/alumina mixture was mulled for 15 additional minutes. The extrusion mix had an LOI of 43.5%. The 90:10 zeolite/alumina mixture was transferred to the 1.0 inch Bonnot extruder and extruded using a stainless steel die plate with 1/16" holes.

Catalyst C

This example demonstrates preparation of a catalyst of the invention. Catalyst C was prepared using 1 weight percent acetic acid and 1 weight percent citric acid.

The Lancaster mix muller was loaded with 645 grams of ammonium-ferrierite (5.4% LOI) and 91 grams of CATAPAL® D alumina (LOI of 25.7%). The alumina was blended with the ferrierite for 5 minutes during which time 152 milliliters of de-ionized water was added. A mixture of 6.8 grams glacial acetic acid, 7.0 grams of citric acid and 152 milliliters of de-ionized water was added slowly to the muller in order to peptize the alumina. The mixture was mulled for 10 minutes. 0.20 Grams of tetraammine palladium nitrate in 153 grams of de-ionized water were then added slowly as the mixture was mulled for a period of 5 additional minutes. Ten grams of METHOCEL®(R) F4M hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a stainless steel die plate with 1/16" holes.

Catalyst D

Catalyst D was prepared as a comparative example using 2 weight percent citric acid and no monocarboxylic acid or inorganic acid in the catalyst preparation.

The Lancaster mix muller was loaded with 645 grams of ammonium-ferrierite (5.4% LOI) and 91 grams of CATAPAL® D alumina (LOI of 25.7%). The alumina was blended with the ferrierite for 5 minutes during which time 155 milliliters of de-ionized water was added. A mixture of 14.0 grams of citric acid and 154 milliliters of de-ionized water was added slowly to the muller in order to peptize the alumina. The mixture was mix-mulled for 10 minutes. 0.20 Grams of tetraammine palladium nitrate in 155 grams of de-ionized water were then added slowly as the mixture was mulled for a period of 5 additional minutes. Ten grams of METHOCEL®(R) F4M hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a stainless steel die plate with 1/16" holes.

Catalyst E

This example demonstrates preparation of a catalyst using 1 weight percent acetic acid and 1 weight percent glycolic acid in the preparation of the catalyst.

The Lancaster mix muller was loaded with 598 grams of ammonium-ferrierite (14.9% LOI) and 76 grams of CATAPAL® D alumina (LOI of 25.7%). The alumina was blended with the ferrierite for 5 minutes during which time 107 milliliters of de-ionized water was added. A mixture of 5.7 grams glacial acetic acid, 5.7 grams of glycolic acid and 107 milliliters of de-ionized water was added slowly to the muller in order to peptize the alumina. The mixture was mulled for 10 minutes. 0.167 Grams of tetraammine palladium nitrate in 107 grams of de-ionized water were then added slowly as the mixture was mulled for a period of 5 additional minutes. Ten grams of METHOCEL®(R) F4M hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a stainless steel die plate with 1/16" holes.

Catalyst F

This example demonstrates preparation of a catalyst of the invention. Catalyst F was prepared using 1 weight percent acetic acid and 1 weight percent tartaric acid.

The Lancaster mix muller was loaded with 598 grams of ammonium-ferrierite (14.9% LOI) and 76 grams of CATAPAL® D alumina (LOI of 25.7%). The alumina was blended with the ferrierite for 5 minutes during which time 107 milliliters of de-ionized water was added. A mixture of 5.7 grams glacial acetic acid, 5.7 grams of D,L-tartaric acid and 107 milliliters of de-ionized water was added slowly to the muller in order to peptize the alumina. The mixture was mix-mulled for 10 minutes. 0.167 Grams of tetraammine palladium nitrate in 107 grams of de-ionized water were then added slowly as the mixture was mulled for a period of 5 additional minutes. Ten grams of METHOCEL®(R) F4M hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a stainless steel die plate with 1/16" holes.

Extrudate Drying and Calcination

All of the above moist extrudates (Catalysts A–F) were dried at 125° C. for 16 hours. After drying, the extrudates were longsbroken manually. The extrudates were calcined in flowing air at 200° C. for two hours and at a maximum temperature of 500° C for two hours. The extrudate was allowed to cool in a nitrogen filled desiccator before loading into the reactors.

Testing Procedure

Isomerization

A stainless steel tube, 1 inch OD, 0.6 inch ID and 26 inches long was used as a reactor. A thermowell extended 20 inches from the top of the tube. To load the reactor, it was first inverted and a small plug of glass wool was slid down the reactor tube over the thermowell until it hit the bottom of the tube. Silicon carbide (20 mesh) was added to a depth of about 6 inches. Over this was placed a small plug of glass wool. Approximately 4 grams of catalyst particles, 6–20 mesh, admixed with about 60 grams of fresh silicon carbide (60–80 mesh) were added in two parts to distribute the catalyst evenly. The 1.5 catalyst bed was typically about 10 inches long. Another piece of glass wool was added to the top of the catalyst and the reactor was topped with 20 mesh silicon carbide, followed by a final plug of glass wool. A multipoint thermocouple was inserted into the thermowell and was positioned such that the temperature above, below and at three different places in the catalyst bed could be monitored. The reactor was inverted and installed the furnace.

The feed utilized was 1-butene obtained from Scott Specialty Gases with a 1-butene content of greater than 99.2% weight. The 1-butene was fed to the reactor in the gas phase.

To start up the reactor, it was first heated to the desired operating temperature over a four hour period and held at the operating temperature for 2 hours, all under flowing nitrogen. After this pretreatment, the nitrogen flow was shut off and the 1-butene was added at a rate to give a feed rate of 36 g/hr, weight hourly space velocity of 9.0 hr$^{-1}$. The reactor was operated at an outlet pressure of 3 psig and at a temperature of 430° C.

Calculations

Conversion and selectivity are calculated for each sample during testing runs and used for comparison of the various catalysts. Therefore the calculation of conversion and selectivity reflect the feed (FD) and effluent (EFF) concentrations of butene-1 (B1) and butene-2 (B2) and isobutylene (IB1). Conversion is calculated as:

$$\% \text{ Conversion} = \frac{(wt \% B1 + wt \% B2)FD - (wt \% B1 + wt \% B2)EFF}{(wt \% B1 + wt \% B2)FD} \times 100$$

selectivity is calculated as:

$$\% \text{ Selectivity} = \frac{(wt \% IB1)EFF - (wt \% IB1)FD}{(wt \% B1 + wt \% B2)FD - (wt \% B1 + wt \% B2)EFF} \times 100$$

and yield is calculated as $$\% \text{ Yield} = \frac{(wt \% IB1)EFF - (wt \% IB1)FD}{(wt \% B1 + wt \% B2)FD} \times 100$$

Table 1 shows the results of the testing of the various catalysts prepared above. This Table provides the hours of run life of the catalyst in the isomerization process. "Run life" (in hours) is defined herein as the time from start-of-run to the time at which the concentration of methyl branched isoolefin in the product has declined to 33 wt. % after having reached its peak. The Table also provides the selectivity of the catalyst at 40% conversion, 45% conversion and 50% conversion and the highest concentration (weight percent) of methyl branched isoolefin (isobutylene) in the product during the testing.

TABLE 1

| Catalyst | wt % HOAC | wt % Polycarboxylic Acid | % Selectivity at a Fixed Conversion | | | Run life (Hrs) to 33 wt % IB in product | Max IB in product during run |
| --- | --- | --- | --- | --- | --- | --- | --- |
| | | | 40% | 45% | 50% | | |
| A | 1 | 0 | 83 | 78 | 69 | 85 | 35.2 |
| B | 2 | 0 | 80 | 73 | 65 | 65[1] | 32.8 |
| C | 1 | 1 citric | 88 | 83 | 74 | 217 | 38.2 |
| D | 0 | 2 citric | 87 | 82 | 72 | 169 | 37.5 |
| E | 1 | 1 glycolic | 84 | 80 | 69 | 82 | 36.4 |
| F | 1 | 1 tartaric | 89 | 82 | 72 | 183 | 37.4 |

[1]Catalyst never achieved 33 wt % isobutylene in the product under the test conditions. The maxium isobutylene in the product was 32.8 wt % at 65 hours runtime.

AS can be seen from Table 1, the catalyst in which both acetic acid and citric acid was used in the preparation of the catalyst (Catalyst C) exhibited a run length that was roughly 3 times greater than obtained with the catalyst with only acetic acid was used (Catalyst A and B). As can be seen further from Table 1, Catalyst C exibits significantly longer run length and higher isobutylene yield (i.e., higher concentration of isobutylene in the product) then the catalyst in which only citric acid was used (Catalyst D). Further, selectivity to isobutylene at the measured conversion levels for Catalyst C was found to be higher when compared to Catalyst A and B. For example, Catalyst C achieved a selectivity to isobutylene at 40% conversion of 88% compared to 80–83% obtained by Catalysts A and B. Other combinations of acids such as those used in the preparation of Catalysts E and F also resulted in improved skeletal olefin isomerization performance when compared to that of Catalyst B.

Catalyst Properties

The catalysts in the above examples were all 90 weight percent zeolite and 10 weight percent alumina (anhydrous solids basis). Some of the physical properties of the catalysts are listed in Table 2.

TABLE 2

| CATALYST | SURFACE AREA (m²/g) | | | MICROPOREVOLUME (mL/g) |
|---|---|---|---|---|
| | BET | P/Po = 0.03 | LANGMUIR | |
| A | 301 | 358 | 408 | 0.1140 |
| C | 306 | 364 | 417 | 0.1150 |
| D | 304 | 362 | 415 | 0.1148 |

A, C and D have substantially the same crush strength.

We claim:

1. A process for preparing a catalyst for structurally isomerizing a linear olefin of at least 4 carbon atoms to its corresponding methyl branched isoolefin comprising:
   (a) mixing
      (i) a zeolite powder comprising at least one zeolite with at least one one-dimensional pore structure having pore size ranging from greater than 0.42 nm to less than 0.7 nm,
      (ii) an alumina-containing binder,
      (iii) water,
      (iv) from about 0.1 weight percent to about 6 weight percent, based on (i) and (ii), of at least one acid selected from the group consisting of monocarboxylic acids and inorganic acids and,
      (v) from about 0.1 weight percent to about 6 weight percent, based on (i) and (ii), of at least one polycarboxylic acid thereby producing a mixture;
   (b) forming a pellet of said mixture; and
   (c) calcining said pellet at a temperature of from about 200° C. to about 700° C.

2. The process of claim 1 wherein the component (v) in step (a) is an organic acid having at least two carboxylic acid groups and at least one hydroxyl group.

3. The process of claim 1 wherein the component (v) in step (a) is an organic acid having a $C_0$ to $C_{10}$ hydrocarbyl segment and at least two carboxylic acid groups.

4. The process of claim 2 wherein the component (iv) in step (a) is a monocarboxylic acid having substituted or unsubstituted $C_1$ to $C_{20}$ hydrocarbyl group or an inorganic acid.

5. The process of claim 1 wherein the component (v) in step (a) is selected from the group consisting of tartaric acid, citric acid, malic acid, oxalic acid, adipic acid, malonic acid, galactaric acid, 1,2-cyclopentane dicarboxylic acid, maleic acid, fumaric acid, itaconic acid, phthalic acid, terephthalic acid, phenylmalonic acid, hydroxyphtalic acid, dihydroxyfumaric acid, tricarballylic acid, benzene-1,3,5-tricarboxylic acid, isocitric acid, mucic acid and glucaric acid.

6. The process of claim 5 wherein the component (iv) in step (a) is selected from the group consisting of formic acid, acetic acid, glycolic acid and nitric acid.

7. The process of claim 5 wherein the ratio of component (iv) to component (v) in step (a) is within the range of about 1:60 to about 60:1.

8. The process of claim 7 wherein the component (iv) in step (a) is present in an amount from about 0.5 weight percent to about 4 weight percent based on the mixture and the ratio of component (iv) to component (v) is within the range of about 1:10 to about 10:1.

9. The process of claim 8 wherein the alumina-containing binder is selected from alumina, silica-alumina and clay.

10. The process of claim 9 wherein the alumina-containing binder is a high-dispersity alumina.

11. A catalyst composition for structurally isomerizing a linear olefin of at least 4 carbon atoms to its corresponding methyl branched isoolefin produced by the process of claim 1.

12. The catalyst of claim 11 wherein the amount of zeolite powder and alumina-containing powder mixed together is sufficient to provide in the final catalyst form 60 to 99.5 percent by weight of zeolite and from 0.5 to 40 percent by weight of alumina, basis final catalyst.

13. The catalyst of claim 11 wherein the zeolite is a zeolite having a ferrierite isotypic framework structure.

* * * * *